United States Patent [19]

Paoluccio et al.

[11] Patent Number: 4,535,765
[45] Date of Patent: Aug. 20, 1985

[54] LIFESAVING DEVICE

[75] Inventors: John A. Paoluccio, 3530 Kiernan Ave., Modesto, Calif. 95356; Robert Paoluccio, Sacramento, Calif.

[73] Assignee: John A. Paoluccio, Modesto, Calif.

[21] Appl. No.: 511,496

[22] Filed: Jul. 7, 1983

[51] Int. Cl.³ .............................................. A61M 16/00
[52] U.S. Cl. ................................................. 128/203.11
[58] Field of Search ...................... 128/202.28, 202.29, 128/203.11, 205.13, 207.15

[56] References Cited

U.S. PATENT DOCUMENTS

| | | | |
|---|---|---|---|
| 3,017,880 | 1/1962 | Brook | 128/203.11 |
| 3,089,485 | 5/1963 | Hirshhorw | 128/202.28 |
| 3,262,446 | 7/1966 | Stoner | 128/205.13 |
| 3,548,822 | 12/1970 | Seeler | 128/203.11 |

FOREIGN PATENT DOCUMENTS

| | | | |
|---|---|---|---|
| 1309878 | 10/1962 | France | 128/202.28 |
| 1373685 | 8/1964 | France | 128/202.28 |
| 1461526 | 11/1966 | France | 128/202.28 |

Primary Examiner—Henry J. Recla
Attorney, Agent, or Firm—Robert S. Smith

[57] ABSTRACT

Apparatus for facilitating artificial respiration, which includes first, second and third fluid conduits. At least the first and second fluid conduits are axially elongated and each fluid conduit has first and second axial extremities. The first axial extremity of each fluid conduit is disposed in fluid communication with the first axial extremity of each other fluid conduit. A sealing surface is disposed around the second axial extremity of the first and second fluid conduits for cooperation with the lips of the respective users.

20 Claims, 5 Drawing Figures

LIFESAVING DEVICE

BACKGROUND OF THE INVENTION

The invention relates to devices to facilitate lifesaving and particularly to facilitating artificial respiration.

Emergency methods in use today include mouth-to-mouth resuscitation and various direct passage tube structures intended to facilitate mouth-to-mouth resuscitation. The structures include those shown in U.S. Pat. Nos. 3,006,337; 3,013,554; 3,106,916; 3,407,910; and 3,538,913. Mouth-to-mouth resuscitation both with and without such structures has not been wholly satisfactory, in part, because of: (a) the natural repugnance most people have of putting their mouth on a patient's mouth when the patient has vomit or saliva on his mouth, (b) the difficulty of aligning the respective mouths and in maintaining an opening for proper resuscitation to take place, (c) the difficulty of controlling the exhaust air flow rate from the patient while he is exhaling, (d) the lack of confidence most people have giving mouth-to-mouth resuscitation because of a concern that the patient may die, (e) fear of germ transmission, (f) fear of being bitten, (g) the difficulty of maintaining sufficient pressure to seal the respective mouths and the associated problem of resultant injury to the face, lips and teeth of both the patient and the lifesaver, (h) the inclination of many people to avoid various problems by waiting for professional help to arrive with special equipment and this delay may aggravate the patient's condition and may even be fatal in some cases, (i) the awkwardness of the patient's position in some cases, and (j) the lack of all known sanitary features in the existing apparatus so that the the patient's breath, saliva, and possibly vomit can foul the device or contaminate the lifesaver's mouthpiece.

It is an object of the invention is to provide a sanitary, safe, easy-to-use resuscitation device which may be readily utilized to provide mouth-to-mouth resuscitation.

It is still another object of the invention to provide apparatus which overcomes the various problems with the prior art.

SUMMARY OF THE INVENTION

The foregoing objects and other objects and advantages which shall become apparent from the detailed description of the preferred embodiments are attained in apparatus for facilitating artificial respiration, which comprises first, second and third fluid conduits. At least the first and second fluid conduits are axially elongated, each fluid conduit having first and second axial extremities. The first axial extremity of each fluid conduit is disposed in fluid communication with the first axial extremity of each other fluid conduit. A separate means for sealing is disposed around the second axial extremity of the first and second fluid conduits for cooperation with the lips of a user.

The first fluid conduit may have a check valve disposed therein to prevent fluid flow from the second axial extremity to the first axial extremity thereof. The second fluid conduit may have a backflow strainer device. The first axial extremity of the second fluid conduit is configured to depress the tongue of the user in some embodiments. The apparatus may further include a compressible bulb disposed at the first axial extremity of the first fluid conduit, and the bulb may have an inlet check valve allowing flow into the bulb and the bulb expells air through the first fluid conduit when the bulb is squeezed. The second fluid conduit may have the interior surface thereof ridged to minimize flow of saliva out of the mouth of the person being administered artificial respiration. The means for sealing on the second fluid conduit may be movable axially with respect to the fluid conduit to adjust the relative position of the first axial extremity of the second fluid conduit to facilitate depression of the tongue. The third fluid conduit may have a first axial extremity which is open. The means for sealing on the first axial extremity of the second fluid conduit is flexible in some embodiments. The second axial extremity of the second fluid conduit is manufactured of a hard plastic in some embodiments.

BRIEF DESCRIPTION OF THE ACCOMPANYING DRAWING

The invention will be better understood by reference to the accompanying drawing in which.

DESCRIPTION OF THE PREFERRED EMBODIMENT

Figure 1:
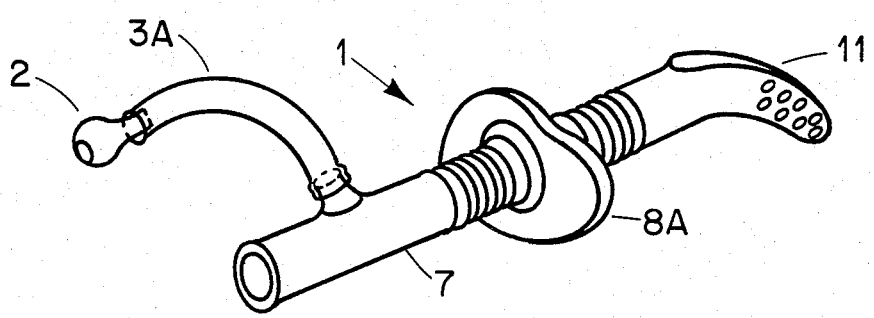
FIG. 1 is an isometric view of a first embodiment of the apparatus in accordance with the invention.
Figure 2:
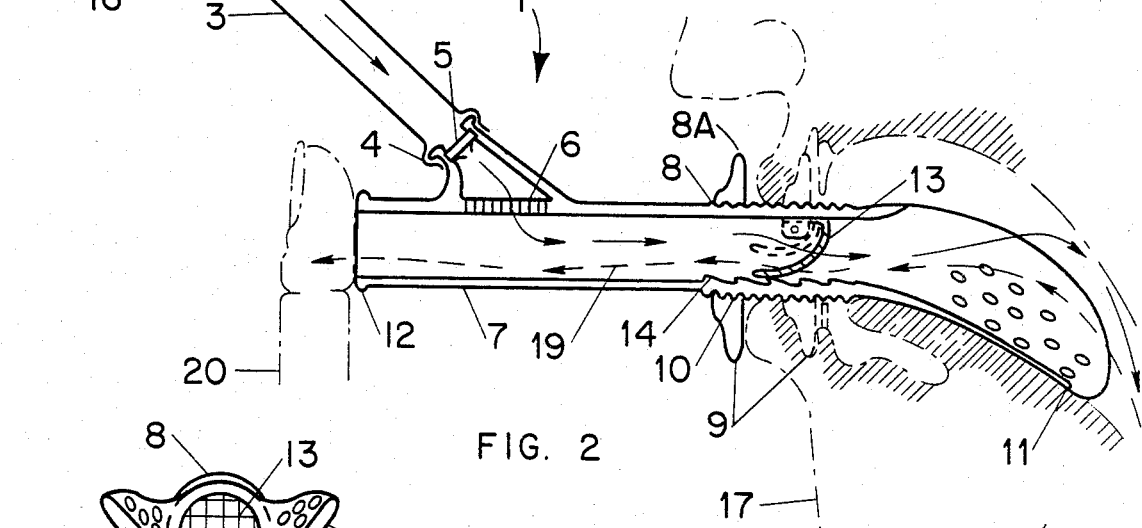
FIG. 2 is a sectional partially schematic view of an embodiment which is substantially identical to the embodiment of FIG. 1.
Figure 4:
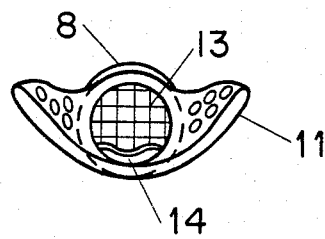
FIG. 4 is a section through the mouthpiece for the patient.
Figure 3:
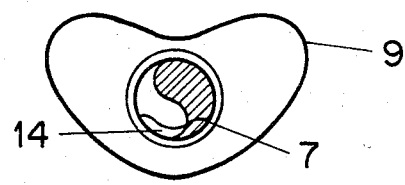
FIG. 3 is a sectional view showing a face seal portion of the apparatus.

Referring now to FIG. 1 there is shown a first embodiment of the invention. FIGS. 2-4 show a substantially identical form of the invention and, thus, the two will be described simultaneously. The only difference is that FIG. 1 shows a curved flexible tube 3A and FIG. 2 shows a straight flexible tube.

It will be understood that the term "lifesaver" is used herein to refer to the person who is giving artificial respiration to a patient or victim 17. A device 1 comprises a mouthpiece 2 for a lifesaver 16 which is connected to a straight flexible tube 3 or a curved flexible tube 3A to a body inlet 4 of the device 1. An inlet valve 5 allows for one-way passage of air 18 through the tube 3 toward the patient 17. The air 18 passes through a strainer 6 which is inside a body 7. Ordinarily the body 7 has a label (not shown) which contains instructions as to the proper adjustment for setting a flexible face piece 8A which is slidable axially along the body 7 into the correct position. The body 7 includes an axial section 8 which extends axially inside the mouth of the patient 17. Bumps or ridges 10 are disposed along the exterior surface of the axial section 8, which serve to hold and position the facepiece 8A and also act to hold the mouth open and form a tough biting surface. The body 7 includes a tongue depressor 11 which not only holds the tongue down, but also provides a large opening for passage of expelled air and debris indicated symbolically by arrows 19. An exit port 12 is provided for expelled air and debris 19 and is positioned so that the air and debris 19 from the patient 17 passes from the area of the tongue depressor 11 to the exit port 12 without passing through the strainer 6. The exit port 12 is shown blocked with a finger 20 of the lifesaver 16 as is appropriate when the lifesaver exhales into the device 1. The finger 20 is released when the patient 17 exhales. The strainer 6 directs any saliva, vomit, or debris 19 to the exit port 12 so as not to interfere with the inlet valve 5 or foul the lifesaver's mouthpiece 2. The device 1 is preferably provided with internal ridges 14 which inhibit saliva backflow toward the patient 17. In some forms of the invention the apparatus may also include a backflow strainer device 13 which fits inside the mouthpiece of the patient 17 and which allows debris 19 to be expelled while allowing air to pass in both directions. Ordinarily the backflow strainer device 13 will be a flexible flapper member having air passageways therein which inhibit return flow of the debris 19 back toward the throat of the patient 17.

Figure 5:
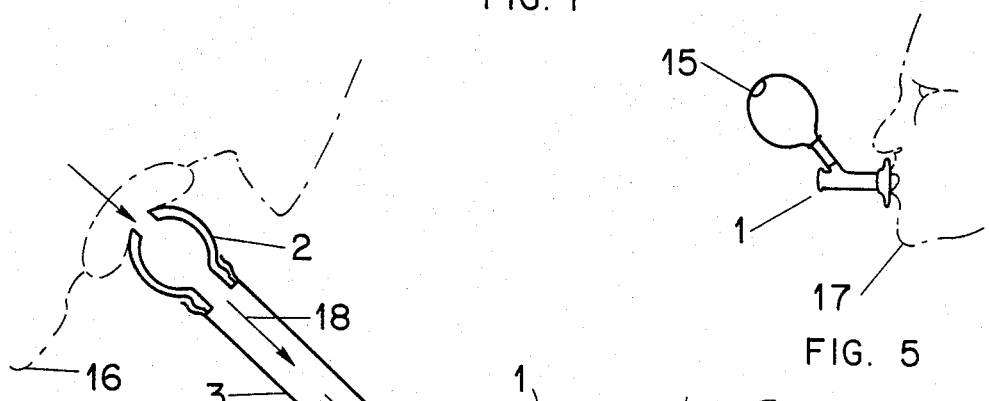
FIG. 5 is an elevational view of a second embodiment of the invention which includes an air bulb with integral check valves.

In another embodiment, illustrated in FIG. 5, the device 1 is fitted with an accessory inlet bulb 15 with an air backflow or check valve so that it could be used for blowing air into the patient's mouth instead of using the lifesaver's breath. The bulb 15 may be of the general type commonly used on atomizers. The lifesaver 16 would merely insert the device 1 and squeeze the accessory inlet bulb 15. The bulb 15 is fitted with a built-in air check valve to allow ambient air to enter the bulb 15 and expel air through the hose or tube 3 when compressed. Several squeezes of the bulb 15 would equal one breath. Air would then enter the patient's mouth and be expelled out the exit port 12 as in the embodiment of FIGS. 1-4. This procedure would be repeated until further treatment is no longer necessary.

The air flow 18 from the lifesaver 16 is shown in FIG. 2 travelling through the device 1 to the patient 17. Expelled air 19 from the patient 17 is shown travelling through the device 1 to the exit port 12. The face seal 9 is also shown pressed against the lips of the patient 17. Alternatively, the face seal 9 is disposed inside the mouth of the patient 17 between the lips and the teeth.

In operation the lifesaver 16 removes the device 1 from case (not shown), which is clearly marked with instructions. The face seal 8A is moved axially along the axial section 8 of the body 7 to the proper insertion length corresponding to the patient's size. The lifesaver 16 then opens the mouth of the patient 17 with the aid of the device 1, if necessary, inspects for debris and inserts the tongue depressor 11 of the device 1. The lifesaver 16 pushes the face seal 8A firmly against the face of the patient 17. The lifesaver 16 then holds one finger 20 over the exit port 12 and exhales into the device 1. The lifesaver 16 can be in any position as long as he can reach the mouthpiece 2, which is preferably mounted by a flexible tube 3A or 3. The lifesaver 16 removes his finger 20 from the exit port 12 to allow the patient 17 to expel air. These steps are repeated again and again until the patient 17 begins normal respiration (or until further treatment is no longer justified). The one-way valve 5 stops the release of air through the mouthpiece 2. Air is only allowed to enter the mouthpiece 2 via the lifesaver 16. Thus, the mouthpiece 2 is kept clean. The exit port 12 ordinarily will be transparent and, thus, will show any debris or vomit being expelled by the patient 17. If the patient 17 should vomit, the clear pathway to the exit port 12 allows for quick and easy expelling of debris. The integral strainer 13 prevents fouling of the one-way valve 5 or the lifesaver's mouthpiece 2.

The tongue depressor 11 is broader than other axial portions of the body 7 to facilitate depressing the tongue of the patient 17 and to aid in opening the breathing passage and is ordinarily constructed of transparent, flexible plastic. The tongue depressor 11 is perforated to avoid blocking any air flow and to allow saliva to enter. The internal ridges or notches 14 are provided to allow for easy flow outward of saliva while inhibiting return flow, thus minimizing gagging. The exterior ridges 10 provide a tough bite surface for the patient's teeth and also provide detents for the face seal 8A so that adjustment is maintained. The internal backflow prevention strainer 13 is provided to allow the debris and vomit 19 to be expelled by the patient 17, but prevents backflow. The strainer 13 configuration does not, however, interfere with air flow in either position.

The mouthpiece 2 for the lifesaver 16 is maintained in a sanitary state because the patient's breath is expelled through the exhaust port 12 along with saliva, debris and vomit 19. Expelled air cannot pass through the air backflow valve 5 to the lifesaver's mouthpiece 2. The flexible hose 3 allows the lifesaver 16 to be in any position and still use the mouthpiece 2.

The face seal 8A can be adjusted to fit any patient 17 regardless of his or her size. In other words, the apparatus is suitable for use with large people as well as small children.

The device 1 encourages all persons to act in an emergency by giving them self-confidence and is a valuable aid in applying mouth-to-mouth resuscitation. This device 1 can also be used on a choking victim. In addition, it may be carried by persons subject to epileptic seizures or by those who have foreseeable breathing problems.

The invention is also advantageous because the lifesaver's mouth does not come into direct contact with the patient's mouth. Therefore, neither the patient 17 nor the lifesaver 16 transmits germs. The lifesaver 16 cannot be bitten. Anyone can feel confident using the device 1 because the use is so simple. There is no need to wait for professional help to arrive with special equipment.

The lifesaver 16 can accommodate the patient 17 in almost any position as long as he can reach the flexible mouthpiece 2. The face seal 8A is soft and pliable and, thus quickly forms a tight seal. The tongue depressor 11 constantly holds down the tongue of the patient 17. The tough section of the mouthpiece 2, which is inserted just inside the mouth, serves to hold the teeth apart and prevents the patient 17 from biting his tongue or the lifesaver 16. It also permits free flow of air or debris. The device 1 prevents physical damage to the face, lips and teeth of both the lifesaver 16 and the patient 17 and can easily be carried by persons subject to breathing failure. The device 1 can be utilized in first-aid kits for homes and businesses, public buildings and transportation, automobiles, and eating facilities. The device 1 can be mass produced and constructed of sturdy plastic, therefore keeping the cost extremely low.

Although the invention has been described in terms of a flexible tube 3 or flexible hose 3A cooperating with a body 7, it will be understood that the illustrated embodiment may be considered to be interconnected first, second and third fluid conduits and that the fluid conduit having an opening for cooperation of the finger 20 of the user may have an axial dimension approaching an infinitely small dimension. It will also be understood that any two of these fluid conduits may be coaxial and the axis of each fluid conduit may be rectilinear.

The invention has been described with reference to its illustrated preferred embodiment. Persons skilled in the art of constructing lifesaving equipment may, upon exposure to the teachings herein, conceive variations in the mechanical development of the components therein. For example, in various forms of the invention the device may be fitted with mouthpieces 11 of various shapes. Such variations are deemed to be encompassed by the disclosure, the invention being delimited only by the appended claims.

Having thus described my invention, I claim:

1. Apparatus for facilitating administration of mouth to mouth artificial respiration to a patient, which comprises:

first, second and third fluid conduits, at least said first and second fluid conduits being axially elongated, each fluid conduit having first and second axial extremities, said first axial extremity of each fluid conduit being connected together and in fluid communication with said first axial extremity of each other fluid conduit;

means for sealing disposed around said second axial extremities of said first and second fluid conduits for cooperation with the respective lips of the patient and the person administering artificial respiration; and means for substantially preventing back flow of debris into the mouth of a patient, said means comprising a flapper member hingedly mounted in said first fluid conduit to permit free flow in said first fluid conduit from said second to said first axial extremity thereof and having air passageways therethrough to substantially prevent said back flow in the reverse direction.

2. The apparatus as described in claim 1, wherein: said first fluid conduit has a check valve disposed therein to prevent fluid flow from said second axial extremity to said first axial extremity thereof.

3. The apparatus as described in claim 2, wherein: said means for sealing on said second fluid conduit is movable axially with respect to said second fluid conduit.

4. The apparatus as described in claim 3, wherein: said third fluid conduit has a first axial extremity which is open.

5. The apparatus as described in claim 2, wherein: said means for substantially preventing backflow of debris includes a strainer.

6. The apparatus as described in claim 5, wherein: said means for sealing on said second fluid conduit is movable axially with respect to said second fluid conduit.

7. The apparatus as described in claim 6, wherein: said third fluid conduit has a first axial extremity which is open.

8. The apparatus as described in claim 5, wherein: said means for substantially preventing backflow of debris is disposed in said second fluid conduit.

9. The apparatus as described in claim 8, wherein: said second axial extremity of said second fluid conduit is configured to depress the tongue of the user.

10. The apparatus as described in claim 9, further including:
a compressible bulb disposed in fluid communication with said second axial extremity of said first fluid conduit, said compressible bulb having an inlet check valve allowing flow into said bulb and said bulb expelling air through said first fluid conduit when said bulb is squeezed.

11. The apparatus as described in claim 10, wherein: said second fluid conduit has ribs disposed on at least an axial portion of the interior surface thereof to minimize flow of saliva out of the mouth of the person being administered artificial respiration, said ribs being disposed proximate to the axial midsection of said second fluid conduit.

12. The apparatus as described in claim 11, wherein: said means for sealing on said second fluid conduit is movable axially with respect to said first fluid conduit.

13. The apparatus as described in claim 12, wherein: said third fluid conduit has a first axial extremity which is open.

14. The apparatus as described in claim 13, wherein: said means for sealing on said second axial extremity of said second fluid conduit is flexible.

15. The apparatus as described in claim 14, wherein: said second axial extremity of said second fluid conduit is manufactured of a hard plastic.

16. The apparatus as described in claim 1, wherein: said second axial extremity of said second fluid conduit is broader than other axial portions thereof to facilitate depressing the tongue of the user.

17. The apparatus as described in claim 1, further including:
a compressible bulb disposed at said second axial extremity of said first fluid conduit, said compressible bulb having an inlet check valve allowing flow into said bulb and said bulb expelling air through said first fluid conduit when said bulb is squeezed.

18. The apparatus as described in claim 17, wherein: said second fluid conduit has the interior surface thereof ridged to minimize flow of saliva into the mouth of the person being administered artificial respiration.

19. The apparatus as described in claim 1, wherein: said means for sealing on said second fluid conduit is movable axially with respect to said fluid conduit to adjust the relative position of said second axial extremity of said second fluid conduit.

20. The apparatus as described in claim 19, wherein: said third fluid conduit has a first axial extremity which is open.

* * * * *